United States Patent [19]
Fischer

[11] Patent Number: 5,618,273
[45] Date of Patent: Apr. 8, 1997

[54] SYRINGE APPARATUS WITH THREADED PLUNGER FOR DELIVERING TOOTH COMPOSITES AND OTHER SOLID YET PLIABLE MATERIALS

[75] Inventor: David V. Fischer, West Jordan, Utah

[73] Assignee: Ultradent Product, Inc., South Jordan, Utah

[21] Appl. No.: 648,481

[22] Filed: May 15, 1996

Related U.S. Application Data

[63] Continuation of Ser. No. 413,198, Mar. 27, 1995, abandoned.

[51] Int. Cl.⁶ .................................................. A61M 5/00
[52] U.S. Cl. ........................ 604/211; 604/218; 222/390
[58] Field of Search ............................ 604/218, 187, 604/208–211, 224; 222/390

[56] References Cited

U.S. PATENT DOCUMENTS

| | | | |
|---|---|---|---|
| 4,189,065 | 2/1980 | Herold | 604/211 X |
| 4,312,343 | 1/1982 | LeVeen et al. | 604/211 |
| 4,710,179 | 12/1987 | Haber et al. | 604/211 |
| 5,318,544 | 6/1994 | Drypen et al. | 604/210 |

*Primary Examiner*—John D. Yasko
*Attorney, Agent, or Firm*—Workman Nydegger Seeley

[57] ABSTRACT

A syringe apparatus is disclosed for delivering solid, yet pliable materials, such as dental composites. The syringe apparatus of the present invention comprises an unthreaded barrel means for containing the material. The unthreaded barrel means has an inlet end, an outlet end, and an enlarged finger grip at the inlet end. The syringe apparatus also comprises means for slidably engaging the finger grip of the barrel means, the engaging means having a threaded throughbore. The syringe apparatus further comprises a plunger means for movement through the barrel means. The plunger means has a threaded portion that is complementary to the threaded throughbore of the engaging means, such that the plunger means may be advanced into the barrel means at the inlet end by applying an external rotational force to the plunger means relative to the barrel means, thereby effecting delivery of the material at the outlet end of the barrel means. Finally, the threaded throughbore of the engaging means and the threaded portion of the plunger means are configured such that the plunger means will automatically withdraw slightly from the barrel means when the external rotational force is removed from the plunger means, reducing the amount of pressure exerted by the plunger means on the material within the barrel means.

18 Claims, 4 Drawing Sheets

SYRINGE APPARATUS WITH THREADED PLUNGER FOR DELIVERING TOOTH COMPOSITES AND OTHER SOLID YET PLIABLE MATERIALS

This application is a continuation of U.S. application Ser. No. 08/413,198, filed Mar. 27, 1995, now abandoned for Syringe Apparatus With Threaded Plunger For Delivering Tooth Composites And Other Solid Yet Pliable Materials.

BACKGROUND

1. Field of the Invention

This invention relates to syringe systems that are used for storing and dispensing materials therefrom, and more particularly to a hand-operated dental syringe that is capable of efficiently storing a solid, yet pliable material, such as a dental composite material or a light activating composite which cures with exposure to an activating light, and extruding precise amounts of the composition from the dental syringe.

2. Prior State of the Art

Various types of syringes have heretofore been used in dental applications, including for storing and dispensing highly viscous or solid, yet pliable dental composites. For example, standard push-type syringes comprising a barrel and a plunger may be used for such purposes. However, especially with solid, yet pliable dental compositions, it is often difficult to generate the pressure needed to express the material through the outlet opening by exerting pressure on the syringe plunger in a longitudinal direction. Another serious problem is that once sufficient pressure is applied to the plunger, it is difficult to precisely control the amount of material expelled through the outlet opening of the barrel, thereby resulting in waste of the excess material.

To overcome some of these problems, syringes having a threaded barrel and a threaded plunger have been used to extrude dental compositions. An example of such a syringe is illustrated in FIG. 1. The syringe 110 comprises a barrel 112 and a plunger 114. Barrel 112 has a central bore 116, an inlet end 118, an outlet end 120, and a threaded insert 122 located at the inlet end 118. The plunger 114 has a proximal end 124, a distal end 126, a threaded stem 128, and a T-shaped head 130. The threads of threaded stem 128 are complementary of, and configured to mate with, the threaded insert 122 of the barrel 112. By inserting the distal end 126 of plunger 114 into threaded insert 122 of barrel 112 and rotating plunger 114 relative to barrel 112 in a clockwise direction, the distal end 126 of plunger 114 is progressively advanced into the central bore 116 of barrel 112. Threaded insert 122 and threaded stem 128 cooperate to translate external rotational forces applied to T-shaped head 130 into longitudinal forces applied through the distal end 126 of plunger 114 to the material contained within the central bore 116 of barrel 112. It will be appreciated by those skilled in the art that the use of the threaded barrel and threaded plunger combination makes it easier for the user to generate the forces needed within barrel 112 to extrude the material out of the outlet end of barrel 112.

However, the threaded syringes found in the prior art have some significant disadvantages. First, such syringes require specially designed and fabricated syringe barrels, which are more difficult and more expensive to manufacture than standard, unthreaded push-type syringe barrels. In addition, such threaded syringe barrels can only be used with threaded plungers and are not, without modification, compatible or interchangeable with standard push-type plungers.

An even more serious disadvantage of the threaded syringes found in the prior art is that they do not provide any means for relieving the pressure built up within the barrel when the external forces are removed from the syringe plunger. As shown in FIG. 1, the prior art syringes typically include relatively fine threads, which result in a relatively high coefficient of friction between the threaded insert 122 of barrel 112 and the threaded stem 128 of plunger 114. Those skilled in the art will appreciate that significant pressures can be generated within barrel 112 as plunger 114 is advanced into barrel 112 by rotating plunger 114 relative to barrel 112, particularly when solid, yet pliable dental compositions are situated within barrel 112. Once the external rotational forces are removed from plunger 114, the fine pitch of the threads coupled with the friction between threaded insert 122 and threaded stem 128 prevent the pressure built up within barrel 112 from forcing plunger 114 to back out from within barrel 112. Instead, the pressure built up within barrel 112 continues to force the dental composition to flow through the outlet end 120 of barrel 112, even after the external forces have been removed from plunger 114, thereby resulting in waste of the excess material.

Yet another disadvantage associated with the threaded syringes found in the prior art is that the fine threads used in such devices collect debris and other contaminants which, in turn, make it more difficult to sterilize and maintain the sterile condition of the device.

BRIEF SUMMARY AND PRINCIPAL OBJECTS OF THE INVENTION

The present invention seeks to resolve the above and other problems which have been experienced in the art. More particularly, the apparatus of this invention constitutes an advancement in syringe art by providing a novel syringe system which achieves each of the objects listed below.

It is an object of the present invention to provide a syringe apparatus that enables the efficient storage and dispensing of solid, yet pliable materials, such as dental composites.

It is another object of the present invention to provide a syringe apparatus that is capable of metering precise amounts of the composite material dispensed therefrom.

It is another important object of the present invention to minimize the waste of the composite material.

It is yet another important object of the present invention to provide a syringe apparatus that automatically relieves the pressure built up within the syringe barrel when the external force is removed from the syringe plunger.

It is an important object of the present invention to provide a syringe apparatus comprising a syringe barrel that can be utilized with either a standard push-type plunger or a threaded, rotation-type plunger.

Yet another object of the present invention is to provide a threaded syringe apparatus that utilizes a standard push-type syringe barrel.

Still yet another object of the present invention is to provide a means for retrofitting a standard push-type syringe barrel for use with a threaded syringe plunger.

Additional objects and advantages of the invention will be set forth in the description which follows and, in part, will be apparent from the description or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the present invention comprises a syringe apparatus of multi-dose capability which enables the removal of material therefrom in a predictable manner. The syringe apparatus of the present invention comprises an unthreaded barrel means for containing the material. The unthreaded barrel means has an inlet end, an outlet end, and an enlarged finger grip at the inlet end. The syringe apparatus also comprises means for slidably engaging the finger grip of the barrel means, the engaging means having a threaded throughbore. The syringe apparatus further comprises a plunger means for movement through the barrel means. The plunger means has a threaded portion that is complementary to the threaded throughbore of the engaging means, such that the plunger means may be advanced into the barrel means at the inlet end by applying an external rotational force to the plunger means relative to the barrel means, thereby effecting delivery of the material at the outlet end of the barrel means. Finally, the threaded throughbore of the engaging means and the threaded portion of the plunger means are configured such that the plunger means will automatically withdraw slightly from the barrel means when the external rotational force is removed from the plunger means, reducing the amount of pressure exerted by the plunger means on the material within the barrel means. Additionally, the syringe apparatus is comprised of materials which block transmissive activating light so as to avoid unwanted exposure of the unextruded light-activating material within the syringe apparatus.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention and the presently understood best mode for making and using the same will be described with additional specificity and detail through the use of the accompanying drawings in which.

DETAILED DESCRIPTION OF THE PREFERRED EMBODIMENTS

Figure 2:
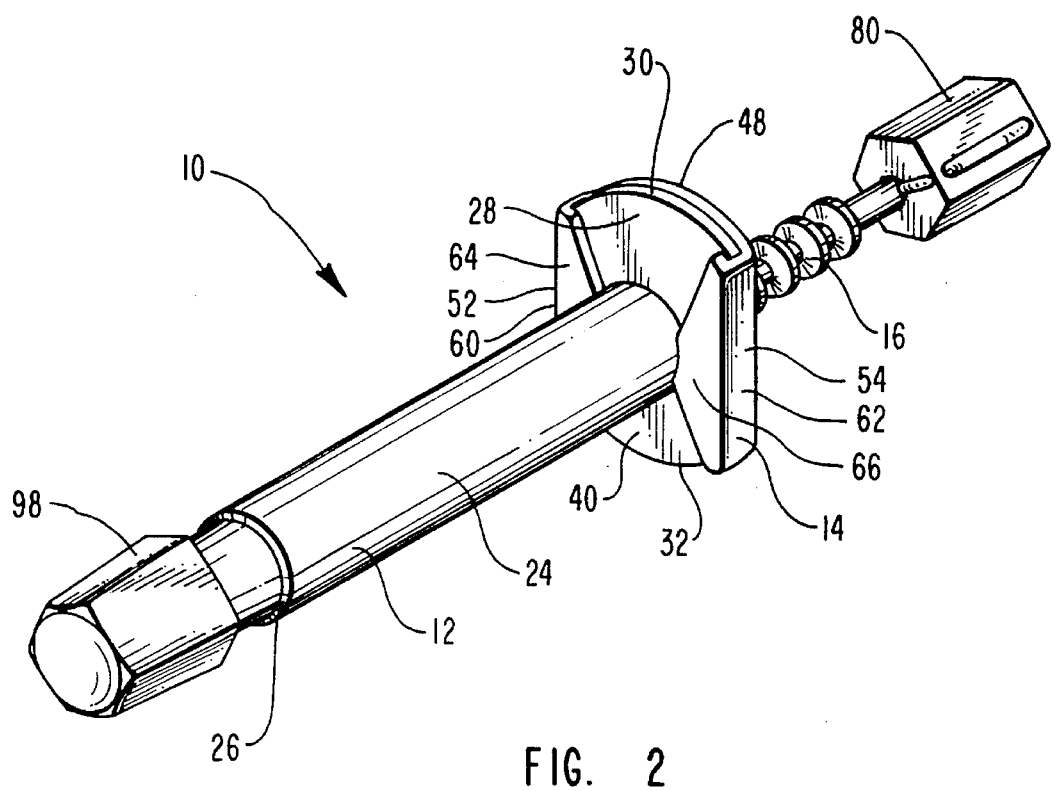
FIG. 2 is perspective view of one presently preferred embodiment of the present invention.
Figure 3:
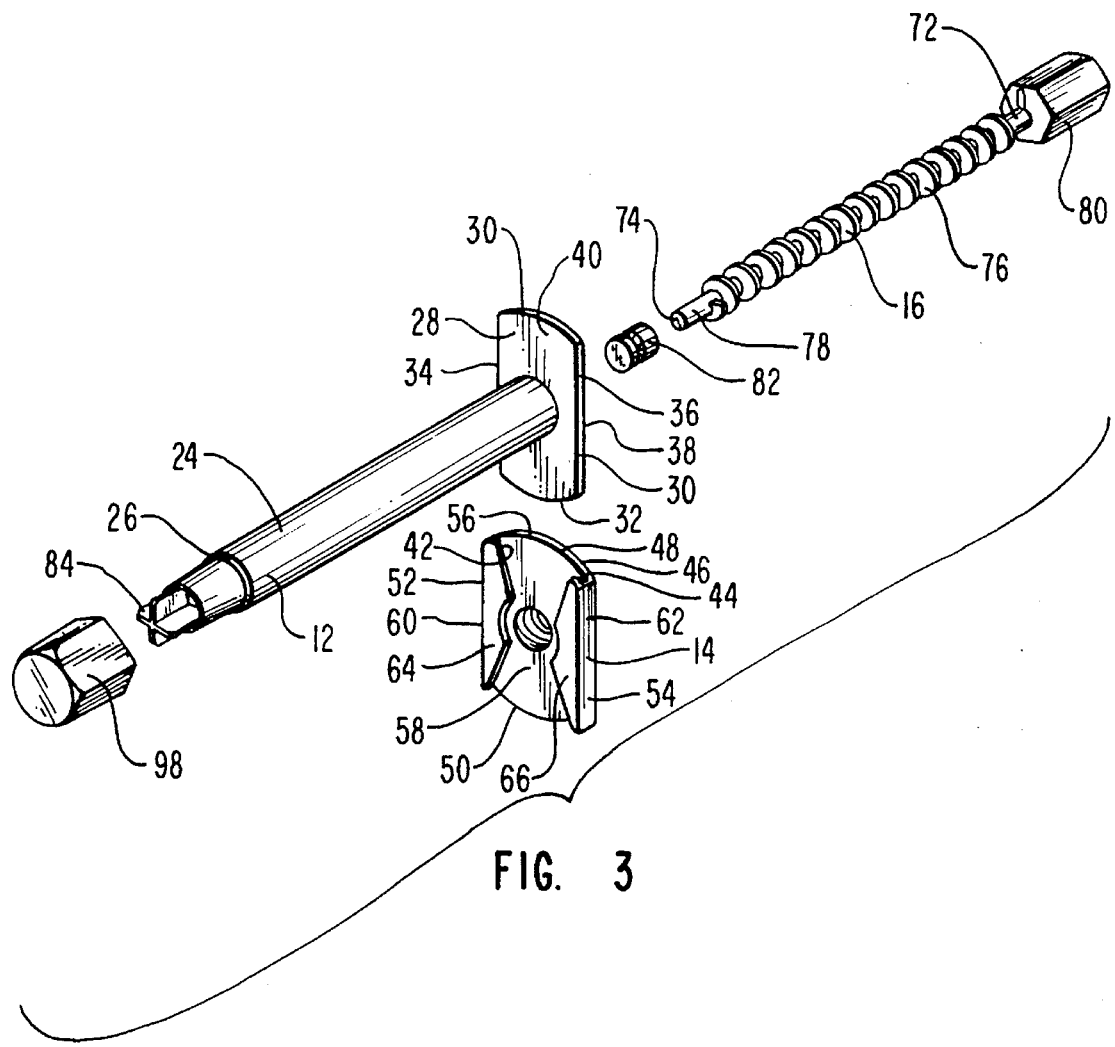
FIG. 3 is an exploded isometric view of one presently preferred embodiment of the present invention.
Figure 4:
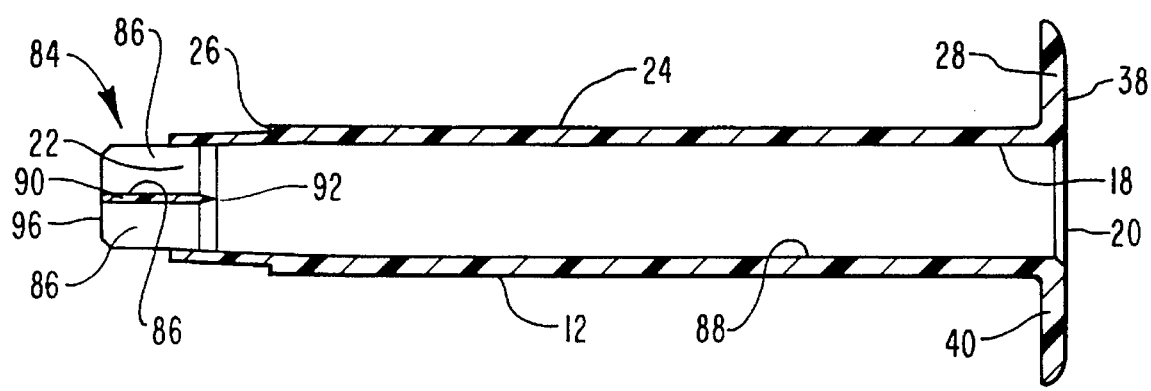
FIG. 4 is a detailed, cross sectional view of one presently preferred embodiment of the syringe barrel of the present invention taken along the center longitudinal axis.

The present invention is broadly described as a syringe apparatus for delivering materials that are highly viscous or essentially solid, yet pliable. Referring generally to FIGS. 2 and 3, the syringe apparatus, generally designated 10, comprises a barrel means 12, a means for slidably engaging the barrel means 14, and a plunger means 16.

Barrel means 12 has a central bore 18, a proximal or inlet end 20, and a distal or outlet end 22. The barrel 12 also has an outer surface 24, which has a smaller outer diameter at distal end 22. Barrel 12 also has a shoulder 26 between distal end 22 and outer surface 24. Barrel 12 terminates at its proximal or inlet end 20 in an integrally formed, enlarged finger grip 28, which is configured to accommodate the fingers of the user when the barrel is used with a standard, nonthreaded push-type plunger (not shown). Finger grip 28 is generally planar and is oriented perpendicular to the longitudinal axis of barrel 12. As best illustrated in FIG. 3, finger grip 28 has rounded sides 30 and 32 located on two opposing sides, and two flat, parallel sides 34 and 36 located on the other two opposing sides. As further illustrated in FIG. 3, the distance across finger grip 28 from flat side 34 to flat side 36 is less than the diameter measured across the rounded sides 30 and 32 of finger grip 28. Further, finger grip 28 provides a generally smooth, planar top surface 38 and a generally smooth, planar bottom surface 40.

As discussed in more detail below, engaging means 14 has slots or channels 42 and 44 configured to receive finger grip 28 of the barrel 12 in mating, press fit relationship. Engaging means 14 has a generally planar portion 46, the shape of which corresponds very closely to the shape of finger grip 28 described above. Planar portion 46 has rounded sides 48 and 50 located on two opposing sides, and two flat, parallel sides 52 and 54 located on the other two opposing sides. Planar portion 46 provides a generally smooth, planar top surface 56 and a generally smooth, planar bottom surface 58. Integrally formed at the outer edges of flat sides 52 and 54 are two side wall portions 60 and 62, which are oriented perpendicular to planar portion 46. Integrally formed at the distal ends of side wall portions 60 and 62 are flanges 64 and 66, which are oriented perpendicular to, and extend inwardly from, side wall portions 60 and 62. Bottom surface 58, side wall portions 60 and 62, and flanges 64 and 66 cooperate to form slots or channels 42 and 44 for receiving the flat sides 34 and 36 of finger grip 42 in sliding, press fit engagement. As further shown in FIG. 3, flanges 64 and 66 are slightly chamfered so as to guide finger grip 42 into engagement with engaging means 14. In addition, the lateral separation between the distal ends of flanges 64 and 66 is slightly less than the outside diameter of barrel 12 adjacent to finger grip 42, so as to provide secure engagement between finger grip 42 and engaging means 14 when finger grip 42 is fully inserted into engaging means 14. Engaging means 14 also has a cylindrical portion 68 situated at the center of top surface 56. Cylindrical portion 68 is formed as an integral part of engaging means 14. A throughbore 70, with internal threads, passes through the center of cylindrical portion 68 and planar portion 46 of engaging means 14. Cylindrical portion 68 and threaded throughbore 70 are situated on engaging means 14 such that they are in longitudinal alignment with the central bore 18 of barrel 12 when engaging means 14 is fully engaged over finger grip 42.

Plunger 16 has a proximal end 72, a distal end 74, a threaded stem 76, an unthreaded distal tip 78, and an integrally formed, hexagonally shaped head 80. The external threads of threaded stem 76 are complementary of, and configured to mate with, the internal threads of the throughbore 70 of the engaging means 14. The outside diameter of the threads of threaded stem 76 is approximately the same, yet is slightly smaller than, the internal diameter of central bore 18 of barrel 12, such that threaded stem 76 will slide with close tolerance within central bore 18.

To prevent the dental composite material from flowing back up between the threads of threaded stem 76 as it is advanced into barrel 12, a cylindrically shaped plug 82 is provided, which receives the unthreaded distal tip 78 of plunger 16 in mating relationship. The outside diameter of plug 82 is approximately the same, yet slightly smaller than, the internal diameter of central bore 18 of barrel 12, such that plug 82 will slide with close tolerance within central bore 18. Plug 82 also has an annular recess for receiving an o-ring of suitable size (not shown) so as to provide a more effective seal against the inner surface of central bore 18. The distal end of plug 82 has a concave surface, which serves to focus the forces applied through the plunger into the center of the material and, at the same time, scrape off any material that may adhere to the inner surface of barrel 12. As will be appreciated, the outside diameter of plug 82 is larger than the inside diameter of the internal threads of throughbore 70 of engaging means 14. Accordingly, plug 82 must be inserted into central bore 18 of barrel 12 prior to sliding engaging means 14 onto finger grip 28. With the dental composition material situated in barrel 12 and plug 82 inserted into the central bore 18 of barrel 12, engaging means 14 is then slid into place over finger grip 28 of barrel 12 in the manner described above.

By inserting the distal end 74 of plunger 16 into threaded throughbore 70 of engaging means 14 and rotating plunger 16 relative to barrel 12 in a clockwise direction, the distal end 74 of plunger 16 is progressively advanced into the central bore 18 of barrel 12. Threaded throughbore 70 and threaded stem 76 cooperate to translate external rotational forces applied to head 80 into longitudinal forces applied through the distal end 74 of plunger 16 to plug 82 and, in turn, through plug 82 to the dental composite material of contained in barrel 12. It will be appreciated by those skilled in the art that the use of the threaded plunger makes it easier for the user to generate the forces needed within barrel 12 to extrude the material out of the outlet end 22 of barrel 12. In that regard, the enlarged head 80 is hexagonally shaped to facilitate ease of gripping and manipulation by the user. The hexagonal shape of head 80 also allows the user efficiently to rotate plunger 16 with a minimal amount of hand and wrist rotation.

Another important feature of the present invention is that it provides a means for automatically relieving the pressure built up within the barrel when the external forces are removed from the syringe plunger. Those skilled in the art will appreciate that significant pressures can be generated within barrel 12 as plunger 16 is advanced into barrel 12 by rotating plunger 16 relative to barrel 12, particularly when solid, yet pliable dental compositions are situated within barrel 12. In prior art devices, the friction between threaded barrel and the threaded plunger prevents the pressure built up within syringe barrel from forcing syringe plunger 16 to back out from within the syringe barrel, even when the external forces applied to the plunger have been removed. Under those conditions, the pressure built up within the syringe barrel continues to force the dental composition to flow out the end of the syringe barrel, resulting in an excessive amount of the material being expressed out the end of the barrel and wasted.

Figure 5:
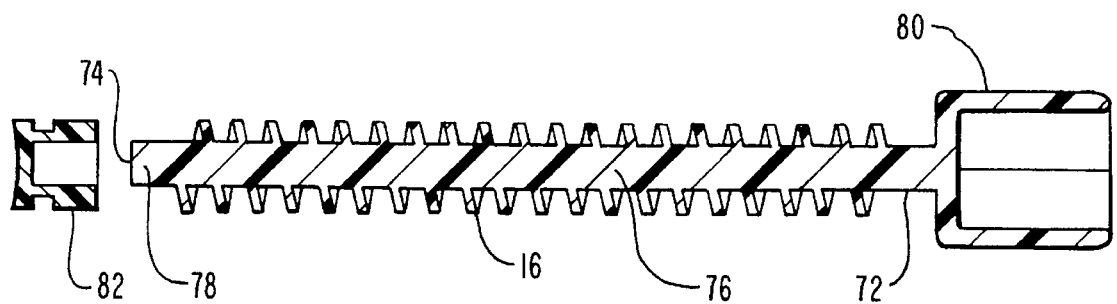
FIG. 5 is a detailed, exploded cross sectional view of one presently preferred embodiment of the syringe plunger and the plunger plug of the present invention.
Figure 6:
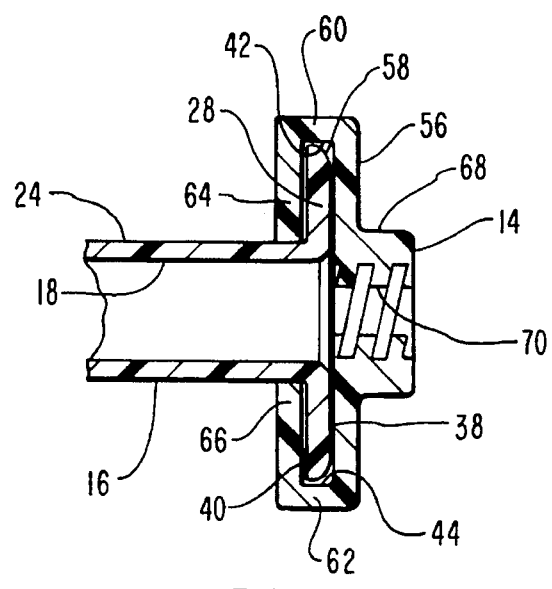
FIG. 6 is a detailed, cross sectional view of the top portion of one presently preferred embodiment of the of the syringe barrel with the attachment means in place, mated with the finger grip of the syringe barrel.

In the present invention, however, the internal threads of throughbore 70 and the external threads of threaded stem 76 have been specially selected and designed to allow plunger 16 automatically to back off slightly, or "snap back," when the external rotational force applied by the user is removed from plunger 16. As best illustrated in FIGS. 5 and 6, the threads of throughbore 70 and threaded stem 76 are fairly coarse, and the teeth of the threads are generally square-shaped. Those skilled in the art will appreciate that these features combine to present threads with a relatively low coefficient of friction. Accordingly, once the external pressure is removed from plunger 16, the coarse pitch of the threads coupled with the relatively low coefficient of friction allows the pressure built up within barrel 12 to urge or force plunger 16 to withdraw slightly from barrel 12, thereby relieving the pressure and stopping the flow of material out of the outlet end 22 of barrel 12. In one presently preferred embodiment, the pitch of the threads of throughbore 70 and threaded stem 76 is approximately ten threads per inch. Those skilled in the art will appreciate that the "snap back" effect will be even greater with threads that are more coarse, but that must be balanced against the mechanical efficiency of the threads in translating the rotational force applied to the head 80 of plunger 16 into longitudinally oriented forces.

In addition, the number of rotations (or fraction thereof) of plunger 16 relative to barrel 12 provides a means for metering the amount of material expressed from the outlet end 22 of syringe 10. In the presently preferred embodiment incorporating the ten pitch threads, each complete revolution (e.g., 360 degrees) of head 80 causes plunger 16 to advance longitudinally a sufficient distance to force just enough dental composite material out the outlet end 22 of barrel 12 to completely fill the QUADRASPENSE® dispensing tip, which will be discussed in detail below. Head 80 is also provided with a raised longitudinal rib along at least one side thereof, which serves as a reference point to enable the user to monitor or gauge the number of rotations (or fraction thereof) of plunger 16 relative to barrel 12 and, thus, the amount of material dispensed out the outlet end 22 of barrel 12.

The present invention may be used with essentially any type of termination at the outlet end 22 of barrel 12. For example, barrel 12 could terminate at its outlet end in a delivery tip of the type disclosed in U.S. Pat. No. 5,269,684. Alternatively, barrel 12 could terminate at its outlet end in a simple opening, luer fitting or other type of fitting commonly used at the distal end of dental or medical syringes through which the dental composite material is extruded. The present invention is not limited to any specific type of termination.

Figure 7:
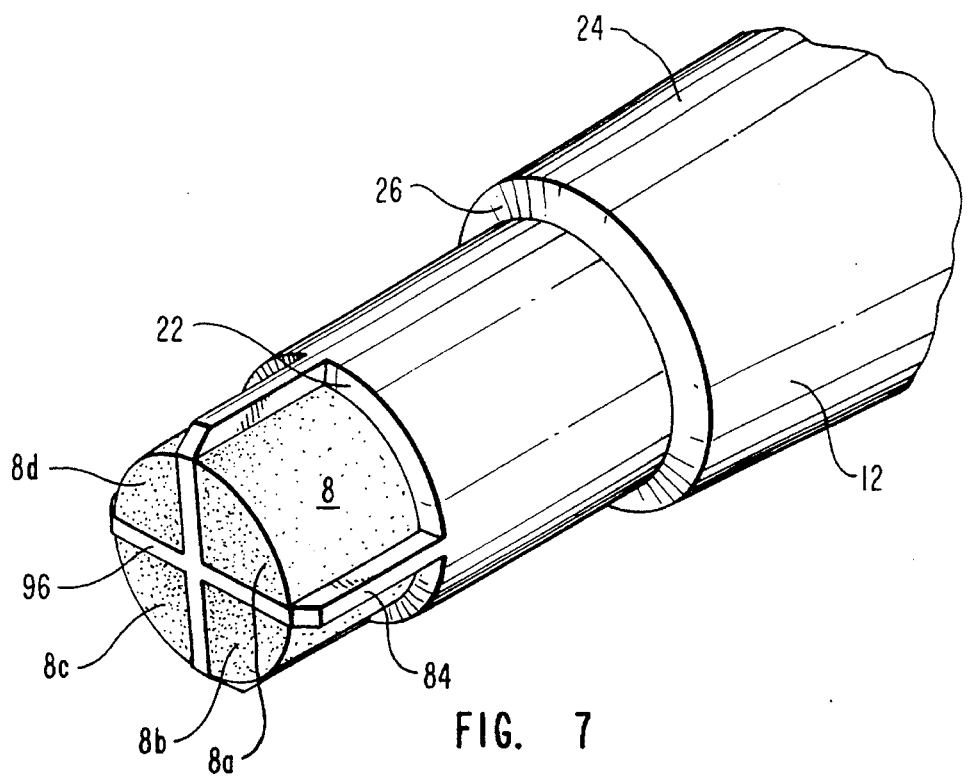
FIG. 7 is a detailed perspective view of a portion of one presently preferred embodiment of the outlet end of the syringe barrel.
Figure 8:
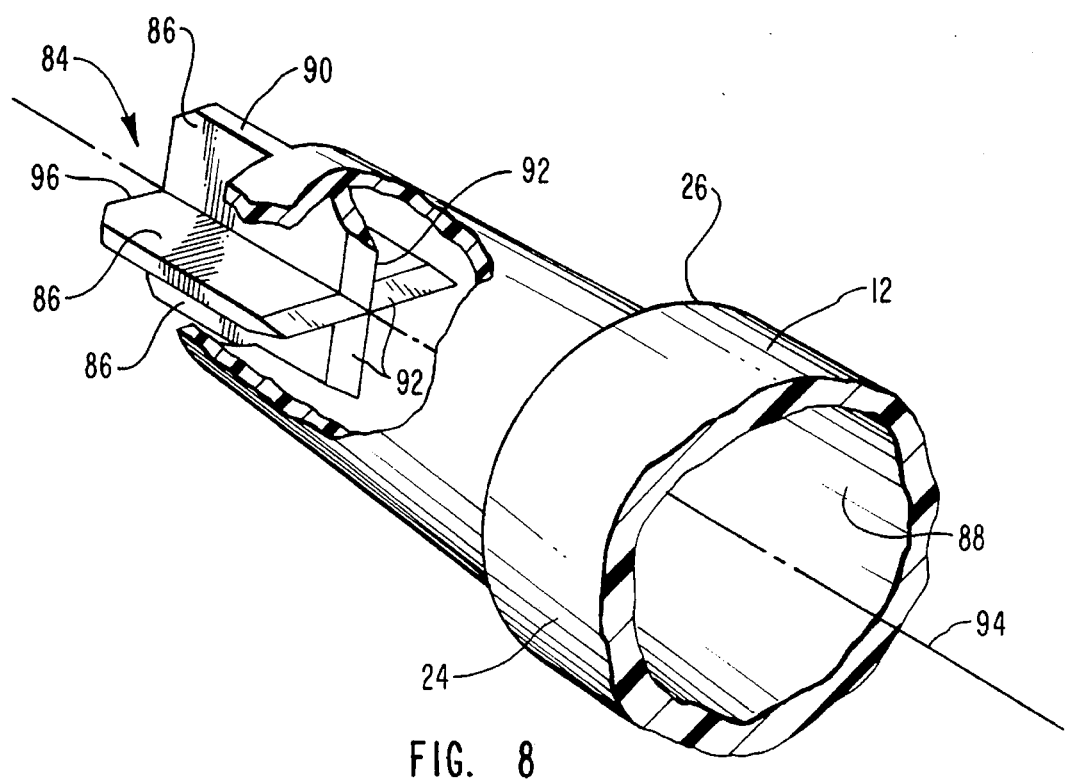
FIG. 8 is a detailed perspective view, with partial cutaway, of one presently preferred embodiment of the outlet end of the syringe barrel.

In one presently preferred embodiment of the invention, the syringe apparatus 10 terminates at its outlet end in a QUADRASPENSE®delivery tip of the type disclosed in U.S. Pat. No. 5,387,103. As illustrated in FIGS. 3, 7 and 8, barrel 16 further comprises a divider means 84 for sectionalizing and individually compartmentalizing the sectionalized portions 8a, 8b, 8c and 8d of the material 8. As shown best in FIG. 7, the material 8 becomes sectionalized and individually compartmentalized as the plunger 16 pushes the material 8 to the outlet end 22 of the barrel 12. In a presently preferred embodiment, the net result of the action between the barrel 12 and its associated divider means with the plunger 16 is that the material 8 will be presented beyond the outlet end 22 of the barrel 12 in a plurality of individualized sections 8a, 8b, 8c and 8d. Each of the individualized sections 8a, 8b, 8c and 8d of the material 8 is contained in a separate compartment. Each separate compartment has a support surface 86 which extends beyond the outlet end 22 of the barrel 12. Each section of material 8a, 8b, 8c and 8d lies within a compartment formed by the inside surface 88 of the barrel 12, and at least one support surface 86 of a cutting plate 90. Cutting plates 90 are shown as radially disposed vanes. Each separate compartment accommodates the removal of a selected portion 8a, 8b, 8c and/or 8d of the sectionalized and compartmentalized part of the material 8 in the manner discussed in detail in U.S. Pat. No. 5,387,103.

As best illustrated in FIG. 8, the divider means comprises several cutting plates 90, having on each such cutting plate 90 a support surface 86. Each cutting plate 90 has a leading beveled edge 92, which serves to cut the pliable material 8 into individualized sections 8a, 8b, 8c and 8d. In a presently preferred embodiment, each of the cutting plates 90 radially extend from a single longitudinal axis 94. The longitudinal axis 94 from which the cutting plates 90 radiate may be centered relative to the center of the barrel 12, or may be offset if unequal volumes of sectionalized material are desired. Preferably, the leading beveled edge 92 of each cutting plate 90 lies and is situated within barrel 12. Each cutting plate 90 also includes an opposite trailing edge 96 which extends beyond the outlet end 22 of barrel 12.

The cutting plates are shown as being an integrally molded portion of barrel 12. However, those of skill in the art will note that other ways exist of installing a divider means. It is also noted that the cutting plates 90 are concentric with the barrel 12. It is intended that radially disposed cutting plates 90 extend from the longitudinal axis 94 that is shared with the barrel 12 to the inside surface of the barrel 12, such that substantially all of the material 8 that is within barrel 12 will be divided into compartmentalized and sectionalized pieces 8a, 8b, 8c and 8d.

Figure 1:
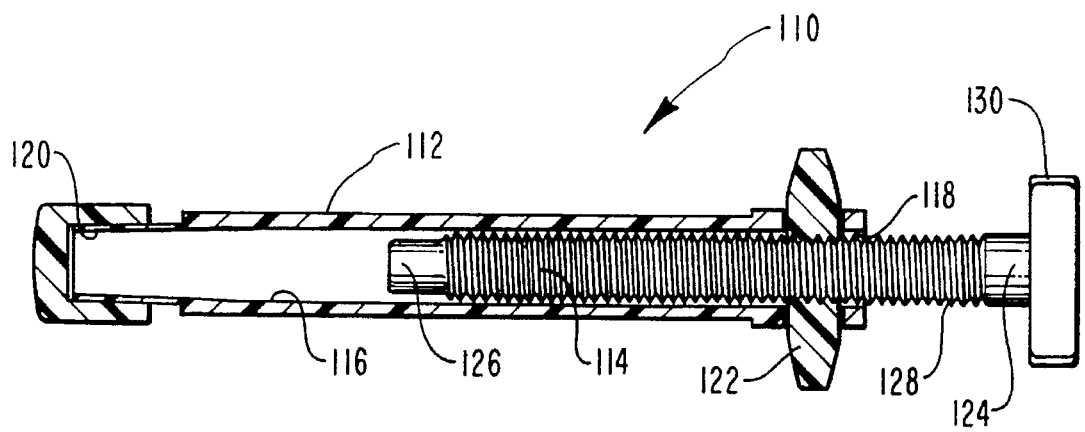
FIG. 1 is a cross sectional view of an assembled prior art device, taken along the center longitudinal axis.

The syringe apparatus 10 further includes a cap means 98 that can be selectively removable from, and placed over, the individualized sections 8a, 8b, 8c and 8d of the pliable material 8 which have been presented beyond the outlet end 22 of the barrel 12. FIG. 1 shows the cap 98 installed at the outlet end 22 of the barrel 12. FIG. 1 further shows the cap 98 fitting tightly at its proximal end against the shoulder 26 of barrel 12. The tight fit between the proximal end of cap 98 and the shoulder 26 of barrel 12 is to ensure that the composite material within the barrel 12 is not exposed to ambient conditions. Cap 98 also features a recessed internal surface (not shown) that overlays and covers all compartmentalized individual sections 8a, 8b, 8c and 8d of the composite material 8 which extend beyond the outlet end 22 of barrel 12. FIG. 2 shows the cap 98 having been removed from the outlet end 22 of the barrel 12.

In the presently preferred embodiment, radially spaced cutting plates 90 do not contact the internal recessed surface (not shown) of cap 98 so as to allow ample space for sections 8a, 8b, 8c and 8d when the cap 98 is installed. It is also noted that the cap 98 sealingly fits around the external surface of the distal end 22 of barrel 12 so that the composite material 8 within barrel 12 is sealed off from ambient conditions. In a preferred embodiment of the present invention, the radially spaced cutting plates 90 do not contact the top inside surface of cap 98, but do contact the inside surface 88 of barrel 12.

A preferable and intended use of a presently preferred embodiment of the present invention is that the syringe apparatus 10 will be used to extrude therefrom a tooth composite material of a type that is essentially solid, yet pliable, and which cures when the material is exposed to an activating light. Other applications and uses of the apparatus are also possible, and are intended as within the scope of the present invention. Preferably, the barrel 12, the radially spaced vanes or cutting plates 90, and support surfaces 86, as well as cap 98 will all be constructed of or coated by a substance having a component that blocks transmission of the activating light which causes the tooth composite material 8 therein to begin curing.

In summary, the dental syringe system of the present invention enables the efficient storage and dispensing of solid, yet pliable materials, such as dental composites with a minimum of wasted material. The present invention also provides a syringe apparatus comprising a syringe barrel that can be utilized with either a standard push-type plunger or be retrofitted for use with a threaded, rotation-type plunger. The present invention further provides a syringe apparatus that automatically relieves the pressure built up within the syringe barrel when the external force is removed from the syringe plunger. The dental syringe system also provides discrete and separated doses (or wedges) of a solid but pliable extrudent as the material is extruded from the syringe system. The doses are easily pinched off by a shaping tool against the support surfaces which extend beyond the outlet end of the barrel means. The barrel means, divider means, and cap means block transmissive exposure of the material therein to an activating light so as to prevent premature curing of the light activated material therein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Patent is:

1. A syringe apparatus that is convertible from a standard push-type syringe into a type of syringe apparatus adapted for using a threaded plunger for delivery of a material of a type that is essentially solid, yet pliable, comprising:

unthreaded barrel means for containing the material, the barrel means comprising an inlet end, an outlet end, and an enlarged finger grip at the inlet end;

separate plug means for insertion into the barrel means at the inlet end thereof;

engaging means for slidable attachment over the separate plug means inserted into the barrel means and for slidable attachment to the finger grip of the barrel means so as to non-rotatably engage the finger grip and so as to enclose and hold the separate plug means within the barrel means, the engaging means having a threaded throughbore;

separate plunger means for contacting the separate plug means through the engaging means, and for movement of the plug means through the barrel means, the plunger means having a threaded portion that is complementary to the threaded throughbore of the engaging means such that the plunger means may be advanced into the barrel means at the inlet end by rotating the plunger means through the threaded throughbore of the engaging means, thereby effecting delivery of the material at the outlet end; and wherein the threaded throughbore of the engaging means and the threaded portion of the plunger means are configured such that the plunger means will automatically withdraw slightly from the barrel means when the external rotational force is removed from the plunger means, reducing the amount of pressure exerted by the plunger means on the material within the barrel means.

2. The syringe apparatus as defined in claim 1, wherein the barrel means further comprises divider means for sectionalizing portions of the pliable material as it is pushed through the barrel means, and for individually compartmentalizing the sectionalized portions of the pliable material as it is pushed by the plunger means to the outlet end of the barrel means, such that the pliable material is presented beyond the outlet end of the barrel means in a plurality of individualized sections, each said individualized section being contained in a separate compartment of the divider means, and each said separate compartment having a support surface extending beyond the outlet end of the barrel means to accommodate removal of a selected portion of the sectionalized and compartmentalized part of the material.

3. The syringe apparatus as defined in claim 1, wherein the enlarged finger grip comprises an integrally formed, first generally planar surface, oriented perpendicular to the longitudinal axis of the barrel means and having at least two flat, parallel opposing edges.

4. The syringe apparatus as defined in claim 3, wherein the engaging means comprises a second generally planar surface having at least two flat, parallel opposing sides with integrally formed channels along such at least two flat, parallel opposing sides, the channels being configured to receive the flat, parallel opposing edges of the first generally planar member in sliding, press fit engagement.

5. The syringe apparatus as defined in claim 1, wherein the plunger means comprises a proximal end, a distal end, and a threaded stem located between the proximal end and the distal end, the threaded stem being complementary to the threaded throughbore of the engaging means.

6. The syringe apparatus as defined in claim 5, wherein the threads of the threaded stem and the threads of the threaded throughbore have a low coefficient of friction.

7. The syringe apparatus as defined in claim 5, wherein the threads of the threaded stem and the threads of the threaded throughbore have a pitch of not more than 10 threads per inch.

8. The syringe apparatus as defined in claim 6, wherein the teeth of the threaded stem and the teeth of the threaded throughbore have a generally square-shaped cross section.

9. In a syringe apparatus that is convertible from a standard push-type syringe into a type of syringe apparatus adapted for using a threaded plunger for delivering a material of a type that is essentially solid, yet pliable, said standard syringe having an unthreaded barrel means for containing the material, the barrel means comprising an inlet end, an outlet end, and an enlarged finger grip at the inlet end, the improvement comprising:

separate plug means for insertion into the barrel means at the inlet end thereof;

engaging means for slidable attachment over the separate plug means inserted within the barrel means, and for slidable attachment to the finger grip of the barrel means so as to non-rotatably engage the finger grip and so as to enclose and hold the separate plug means within the barrel means, the engaging means having a threaded throughbore;

separate plunger means for contacting the separate plug means through the engaging means, and for movement of the plug means through the barrel means, said plunger means having a threaded portion that is complementary to the threaded throughbore of the engaging means such that the plunger means may be advanced into the barrel means at the inlet end by rotating the plunger means through the threaded throughbore of the engaging means, thereby effecting delivery of the material at the outlet end; and wherein the threaded throughbore of the engaging means and the threaded portion of the plunger means are configured such that the plunger means will automatically withdraw slightly from the barrel means when the external rotational force is removed from the plunger means, reducing the amount of pressure exerted by the plunger means on the material within the barrel means.

10. The syringe apparatus as defined in claim 9, wherein the enlarged finger grip comprises an integrally formed, first generally planar surface, oriented perpendicular to the longitudinal axis of the barrel means and having at least two flat, parallel opposing edges.

11. The syringe apparatus as defined in claim 10, wherein the engaging means comprises a second generally planar surface having at least two flat, parallel opposing sides with integrally formed channels along such at least two flat, parallel opposing sides, the channels being configured to receive the flat, parallel opposing edges of the first generally planar member in sliding, press fit engagement.

12. The syringe apparatus as defined in claim 11, wherein the threads of the threaded stem and the threads of the threaded throughbore have a low coefficient of friction.

13. The syringe apparatus as defined in claim 11, wherein the plunger means comprises a proximal end, a distal end, and a threaded stem located between the proximal end and the distal end, the threaded stem being complementary to the threaded throughbore of the engaging means.

14. The syringe apparatus as defined in claim 13, wherein the threads of the threaded stem and the threads of the threaded throughbore have a pitch of not more than 10 threads per inch.

15. The syringe apparatus as defined in claim 14, wherein the teeth of the threaded stem and the teeth of the threaded throughbore have a generally square-shaped cross section.

16. The syringe apparatus as defined in claim 9, wherein the barrel means further comprises divider means for sectionalizing portions of the pliable material as it is pushed through the barrel means, and for individually compartmentalizing the sectionalized portions of the pliable material as it is pushed by the plunger means to the outlet end of the barrel means, such that the pliable material is presented beyond the outlet end of the barrel means in a plurality of individualized sections, each said individualized section being contained in a separate compartment of the divider means, and each said separate compartment having a support surface extending beyond the outlet end of the barrel means to accommodate removal of a selected portion of the sectionalized and compartmentalized part of the material.

17. The syringe apparatus as defined in claim 16, wherein the threads of the threaded portion and the threads of the threaded throughbore are such that one complete revolution of the plunger means relative to the barrel means will apply sufficient pressure to the materials within the barrel to extrude a sufficient amount of the material from the outlet end of the barrel to completely fill the compartments formed by the dividing means.

18. A syringe apparatus that is convertible from a standard push-type syringe into a type of syringe apparatus adapted for using a threaded plunger for delivery of a material of a type that is essentially solid, yet pliable, comprising:

unthreaded barrel means for containing the material, the barrel means comprising an inlet end, and outlet end, and an enlarged finger grip at the inlet end, the enlarged finger grip comprising an integrally formed, first generally planar surface, oriented perpendicular to the longitudinal axis of the barrel means and having at least two flat, parallel opposing edges, the barrel means further comprising divider means for sectionalizing portions of the pliable material as it is pushed through the barrel means, and for individually compartmentalizing the sectionalized portions of the pliable material as it is pushed by the plunger means to the outlet end of the barrel means in a plurality of individualized sections, each said individualized section being contained in a separate compartment of the divider means, and each said separate compartment having a support surface extending beyond the outlet end of the barrel means to accommodate removal of a selected portion of the sectionalized and compartmentalized part of the material;

separate plug means for insertion into the barrel means at the inlet end thereof:

engaging means for slidable attachment over the separate plug means inserted into the barrel means and for slidable attachment onto the finger grip of the barrel means so as to non-rotatably engage the finger grip and so as to enclose and hold the separate plug means within the barrel means, the engaging means comprising a second generally planar surface having at least two flat, parallel opposing sides with integrally formed channels along such at least two flat, parallel opposing sides, the channels being configured to receive the flat, parallel opposing edges of the first generally planar member in sliding, non-rotatable press fit engagement, and the engaging means further comprising a threaded throughbore located on the second generally planar surface such that the threaded throughbore is in longitudinal alignment with the barrel means when the finger grip is fully inserted into the engaging means;

separate plunger means for contacting the separate plug means through the engaging means, and for movement of the plug means through the barrel means, the plunger means having a threaded portion that is complementary to the threaded throughbore of the engaging means such that the plunger means may be advanced into the barrel means at the inlet end by applying an external rotational force to the plunger means relative to the barrel means, thereby effecting delivery of the material at the outlet end; and wherein the threaded throughbore of the engaging means and the threaded portion of the plunger means are configured such that the plunger means will automatically withdraw slightly from the barrel means when the external rotational force is removed from the plunger means, reducing the amount of pressure exerted by the plunger means on the material within the barrel means.

* * * * *

UNITED STATES PATENT AND TRADEMARK OFFICE
CERTIFICATE OF CORRECTION

PATENT NO. : 5,618,273
DATED : April 8, 1997
INVENTOR(S) : David V. Fischer

It is certified that error appears in the above-identified patent and that said Letters Patent is hereby corrected as shown below:

On the title page item [73], Asignee, "Product" should be --Products--

Col. 4, line 29, "fiat" should be --flat--

Col. 4, line 30, "fiat" should be --flat--

Col. 4, lines 52, 54, 58, 59 (two occurrences), and Col. 5, line 2, "42" should be --28--

Col. 6, line 59, "16" should be --12--

Col. 7, line 42, "FIG. 1" should be --FIG. 2--

Col. 7, line 43, "FIG. 1" should be --FIG. 2--

Col. 7, line 53, "FIG. 2" should be --FIG. 3--

Figure 6, Reference numeral "16" should be --12--

Signed and Sealed this

Third Day of March, 1998

Attest:

BRUCE LEHMAN

Attesting Officer

Commissioner of Patents and Trademarks